United States Patent
Hallum

(10) Patent No.: US 8,992,414 B2
(45) Date of Patent: Mar. 31, 2015

(54) LEVATOR FOR REPAIR OF PERINEAL PROLAPSE

(75) Inventor: Alton V. Hallum, Tucson, AZ (US)

(73) Assignee: AMS Research Corporation, Minnetonka, MN (US)

(*) Notice: Subject to any disclaimer, the term of this patent is extended or adjusted under 35 U.S.C. 154(b) by 928 days.

(21) Appl. No.: 12/087,534

(22) PCT Filed: Jan. 10, 2007

(86) PCT No.: PCT/US2007/000541
§ 371 (c)(1),
(2), (4) Date: Jul. 9, 2008

(87) PCT Pub. No.: WO2007/081955
PCT Pub. Date: Jul. 19, 2007

(65) Prior Publication Data
US 2009/0062600 A1   Mar. 5, 2009

Related U.S. Application Data

(60) Provisional application No. 60/757,618, filed on Jan. 10, 2006.

(51) Int. Cl.
*A61F 2/00* (2006.01)

(52) U.S. Cl.
CPC .................... *A61F 2/0045* (2013.01)
USPC .......................................... 600/37

(58) Field of Classification Search
USPC ............................... 600/37, 29–31
See application file for complete search history.

(56) References Cited

U.S. PATENT DOCUMENTS

| | | | |
|---|---|---|---|
| 5,840,011 A | 11/1998 | Landgrebe et al. | |
| 6,802,807 B2 | 10/2004 | Anderson et al. | |
| 6,808,486 B1* | 10/2004 | O'Donnell | 600/30 |
| 6,911,003 B2 | 6/2005 | Anderson et al. | |
| 6,971,986 B2 | 12/2005 | Staskin et al. | |
| 7,048,682 B2 | 5/2006 | Neisz et al. | |
| 7,087,065 B2* | 8/2006 | Ulmsten et al. | 606/151 |
| 2002/0072694 A1 | 6/2002 | Snitkin et al. | |
| 2002/0161382 A1* | 10/2002 | Neisz et al. | 606/151 |
| 2003/0023137 A1* | 1/2003 | Gellman | 600/30 |
| 2003/0216814 A1* | 11/2003 | Siegel et al. | 623/23.66 |
| 2003/0220538 A1* | 11/2003 | Jacquetin | 600/37 |
| 2004/0039453 A1* | 2/2004 | Anderson et al. | 623/23.72 |
| 2004/0249473 A1* | 12/2004 | Delorme et al. | 623/23.64 |
| 2005/0245787 A1 | 11/2005 | Cox et al. | |
| 2005/0250977 A1 | 11/2005 | Montpetit et al. | |

(Continued)

FOREIGN PATENT DOCUMENTS

| | | |
|---|---|---|
| DE | 19544162 | 4/1997 |
| KR | 2005-0026378 | 3/2005 |
| WO | WO 03/073960 | 9/2003 |

(Continued)

OTHER PUBLICATIONS

Cervigni et al., "The Use of Synthetics in the Treatment of Pelvic Organ Prolapse," Current Opinion in Urology, vol. 11, pp. 429-435, 2001.

*Primary Examiner* — Catherine B Kuhlman
(74) *Attorney, Agent, or Firm* — Kagan Binder, PLLC

(57) ABSTRACT

Improved methods and apparatuses for treatment of pelvic organ prolapse are provided. A specialized mesh having a shape for effective placement via the ischiorectal fossa is provided, as is a method of use of such a device.

13 Claims, 8 Drawing Sheets

(56) References Cited

U.S. PATENT DOCUMENTS

2005/0277806 A1* 12/2005 Cristalli ............... 600/30
2005/0283189 A1* 12/2005 Rosenblatt ............ 606/216
2006/0130848 A1* 6/2006 Carey ................. 128/830
2006/0229493 A1* 10/2006 Weiser et al. ........... 600/37

FOREIGN PATENT DOCUMENTS

| WO | WO 03/075792 | 9/2003 | |
| WO | WO 2004045457 A1 * | 6/2004 | ........ A61F 2/02 |
| WO | WO 2006/045042 | 4/2006 | |
| WO | WO 2006069078 A2 * | 6/2006 | ........ A61F 13/49 |

* cited by examiner

Pelvis (front view)

Pelvis (sideview)

Mesh placement area

LEVATOR FOR REPAIR OF PERINEAL PROLAPSE

The present non-provisional patent application claims benefit from International Application No. PCT/US2007/000541, having PCT Publication No. WO 2007/081955 A1, which was filed on Jan. 10, 2007, which in turn claims priority under 35 USC §119(e) from U.S. Provisional Patent Application having Ser. No. 60/757,618, filed on Jan. 10, 2006, by Alton V. Hallum, and titled "Levator/Perineal Prolapse Repair," wherein the entirety of said provisional patent application is incorporated herein by reference.

BACKGROUND OF THE INVENTION

1. Field of the Invention

This invention relates to urogenital surgery.

2. Description of the Related Art

Female genital prolapse has long plagued women. It is estimated by the U.S. National Center for Health Statistics that 247,000 operations for genital prolapse were performed in 1998. With the increasing age of the U.S. population, these problems will likely assume additional importance.

The common clinical symptoms of vaginal prolapse are related to the fact that, following hysterectomy, the vagina is inappropriately serving the role of a structural layer between intra-abdominal pressure and atmospheric pressure. This pressure differential puts tension on the supporting structures of the vagina, causing a "dragging feeling" where the tissues connect to the pelvic wall or a sacral backache due to traction on the uterosacral ligaments. Exposure of the moist vaginal walls leads to a feeling of perineal wetness and can lead to ulceration of the exposed vaginal wall. Vaginal prolapse may also result in loss of urethral support due to displacement of the normal structural relationship, resulting in stress urinary incontinence. Certain disruptions of the normal structural relationships can result in urinary retention, as well. Stretching of the bladder base is associated with vaginal prolapse and can result in complaints of increased urinary urgency and frequency. Other symptoms, such as anal incontinence and related bowel symptoms, and sexual dysfunction are also frequently seen with vaginal prolapse.

Anterior vaginal wall prolapse causes the vaginal wall to fail to hold the bladder in place. This condition, in which the bladder sags or drops into the vagina, is termed a cystocele. There are two types of cystocele caused by anterior vaginal wall prolapse. Paravaginal defect is caused by weakness in the lateral supports (pubourethral ligaments and attachment of the bladder to the endopelvic fascia); central defect is caused by weakness in the central supports. There may also be a transverse defect, causing cystocele across the vagina.

Posterior vaginal wall prolapse results in descent of the rectum into the vagina, often termed a rectocele, or the presence of small intestine in a hernia sac between the rectum and vagina, called an enterocele. Broadly, there are four types based on suspected etiology. Congenital enteroceles are thought to occur because of failure of fusion or reopening of the fused peritoneal leaves down to the perineal body. Posthysterectomy vault prolapses may be "pulsion" types that are caused by pushing with increased intra-abdominal pressure. They may occur because of failure to reapproximate the superior aspects of the pubocervical fascia and the rectovaginal fascia at the time of surgery. Enteroceles that are associated with cystocele and rectocele may be from "traction" or pulling down of the vaginal vault by the prolapsing organs. Finally, iatrogenic prolapses may occur after a surgical procedure that changes the vaginal axis, such as certain surgical procedures for treatment of incontinence. With regard to rectoceles, low rectoceles may result from disruption of connective tissue supports in the distal posterior vaginal wall, perineal membrane, and perineal body. Mid-vaginal and high rectoceles may result from loss of lateral supports or defects in the rectovaginal septum. High rectoceles may result from loss of apical vaginal supports. Posterior or posthysterectomy enteroceles may accompany rectoceles.

Several factors have been implicated as being involved in genital prolapse in women. It is thought that individual women have differing inherent strength of the relevant connective tissue. Further, loss of connective tissue strength might be associated with damage at childbirth, deterioration with age, poor collagen repair mechanisms, and poor nutrition. Loss of muscle strength might be associated with neuromuscular damage during childbirth, neural damage from chronic straining, and metabolic diseases that affect muscle function. Other factors involved in prolapse include increased loads on the supportive system, as seen in prolonged lifting or chronic coughing from chronic pulmonary disease, or some disturbance in the balance of the structural support of the genital organs. Obesity, constipation, and a history of hysterectomy have also been implicated as possible factors.

As noted, vaginal prolapse and the concomitant anterior cystocele can lead to discomfort, urinary incontinence, and incomplete emptying of the bladder. Posterior vaginal prolapse may additionally cause defecatory problems, such as tenesmus and constipation. Furthermore, apart from the physical symptoms, vaginal prolapse has been shown to result in a lower quality of life for its sufferers, including feeling less attractive, less feminine, and less sexually attractive.

Vaginal prolapse develops when intra-abdominal pressure pushes the vagina outside the body. In a normal situation, the levator ani muscles close the pelvic floor. This results in little force being applied to the fascia and ligaments that support the genital organs. Increases in abdominal pressure, failure of the muscles to keep the pelvic floor closed, and damage to the ligaments and fascia all contribute to the development of prolapse. In addition, if a woman has a hysterectomy, the vaginal angle may be altered, causing increased pressure at a more acute angle, accelerating the prolapse.

There are generally two different types of tissue that make up the supportive structure of the vagina and uterus. First, there are fibrous connective tissues that attach these organs to the pelvic walls (cardinal and uterosacral ligaments; pubocervical and rectovaginal fascia). Second, the levator ani muscles close the pelvic floor so the organs can rest on the muscular shelf thereby provided. It is when damage to the muscles opens the pelvic floor or during the trauma of childbirth that the fascia and ligaments are strained. Breaks in the fascia allow the wall of the vagina or cervix to prolapse downward.

As noted above, the levator ani muscles close the pelvic floor so the organs can rest on the muscular shelf thereby provided. The levator ani muscles arise from the pubis, the pelvic fascia, and the ischial spine. They insert on the pelvic viscera, coccyx, and the fibrous raphe of the perineum.

When damage has occurred in the levator muscle, most commonly as a result of obstetric injury, the anatomical defect is noted as a tendency towards a vertical elongation of the levator plate. This downward sagging of the levator plate results in the longitudinal enlargement of the levator hiatus with secondary placement of the cervix and upper vagina upon the levator hiatus. With increased intra-abdominal pressure the defective levator plate is no longer supportive of the downward movement of the uterus, cervix and upper vagina, which are resting upon the levator hiatus, and genital prolapse develops. Over a period of time elongation of the uterosacral and cardinal ligaments will result.

The cardinal and uterosacral ligaments form a suspensory mechanism that suspends the vaginal apex but allows for some vertical mobility. In the normal woman the cervix will descend to but not below the plane of the ischial spines. Damage to the cardinal uterosacral ligament complex permits the uterus and upper vagina to telescope downwards, like an inverted sock. Complete failure of the cardinal uterosacral ligament complex will result in a "cervix-first" prolapse.

Anteriorly, the continence mechanism is maintained by the integrity of the sub-urethral hammock and the insertion of pubo-urethral ligaments into the mid urethra. Posteriorly, the perineal body needs to be firm and substantial in size to allow stretching and angulation of the vagina around it. Levator muscle distension can have a significant effect on perineal body descent and future pelvic prolape, as well as prolapse recurrence.

Treatment of vaginal prolapse is uncertain, and generally based on the symptoms of the prolapse. If symptoms are more severe, treatment is commonly by either surgery or pessary. Surgical options might include hysterectomy or by uterus-saving procedures. Such procedures may include abdominal or vaginal access routes. Sacralcolpopexy or sacrospinous fixation may be used. Anterior colporrhaphy is often utilized for treatment of anterior vaginal prolapse. In addition, methods of surgical repair using mesh or biological implants, or a combination thereof, to support the prolapsed organ in its appropriate position, have been developed, and may use either a transobturator or vaginal approach.

Traditional anterior prolapse repairs have a relatively high failure rate. Consequently, mesh or grafts have been used to provide additional support for a traditional repair. However, the typical placement of such augmentation of the levator muscle is through a transvaginal approach, with transvaginal dissection. Such transvaginal dissection can be more difficult for the surgeon and may lead to further failures. Recent studies show that traditional transvaginal approaches for repair of levator muscle laxity result in a greater incidence of dyspaerunia (painful intercourse) as compared to alternative methods. Studies have also shown that traditional mesh repairs of rectocele repair show unacceptably high levels of mesh erosion. These problems, along with problems of recurrence of the rectocele, are likely due in part to ballooning of the levator muscles. Consequently, there is a need for alternative methods and apparatus for augmentative support of repaired levator muscle in cases of pelvic organ prolapse. Thus, the present invention is directed to improving the mesh anchorage in levatorplasty surgery. Such improvement in anchorage should result in greater longevity of the repair, by substantially minimizing ballooning of the levator musculature typically caused by stress events, such as coughing and sneezing.

SUMMARY OF THE INVENTION

The present invention includes novel devices and methods for urological applications, particularly providing levator muscle support for treatment of pelvic organ prolapse. The present invention is directed to a novel approach for treating levator muscle laxity or disruption, in which a tension-free "backstop" is created to support the levator muscle plate, thereby minimizing the force transmitted to the genital-anal hiatus. The support is placed via the ischiorectal fossa. The approach is also amenable to extension for support of the perineum.

This procedure involves the placement of an implant laterally and adjacent to the levator muscles via the ischiorectal fossa in order to restore the levator muscles to a more anatomically normal position. Such an approach has not been described, and provides another level of repair in patients with pelvic organ prolapse, particularly those with descending perineum syndrome and large volume prolapse.

The placement of a broad based implant via the ischiorectal fossa serves to functionally support disrupted or lax levator muscles in order to prevent or limit descent or lateral displacement of these muscles. The surgical approach is also relatively easier than other described approaches, as the space for placement is easier and safer to access. The described approach provides a reliable repair for treatment of a previously difficult-to-treat syndrome, descending perineum syndrome. The method of buttressing the levator muscles may also augment repairs performed in the vesicogenital or rectovaginal spaces.

BRIEF DESCRIPTION OF THE DRAWINGS

A more complete appreciation of the invention and many of the attendant advantages thereof will be readily obtained as the same becomes better understood by reference to the following detailed description when considered in connection with the accompanying drawings, wherein.

DETAILED DESCRIPTION OF THE PREFERRED EMBODIMENTS

Figure 1:
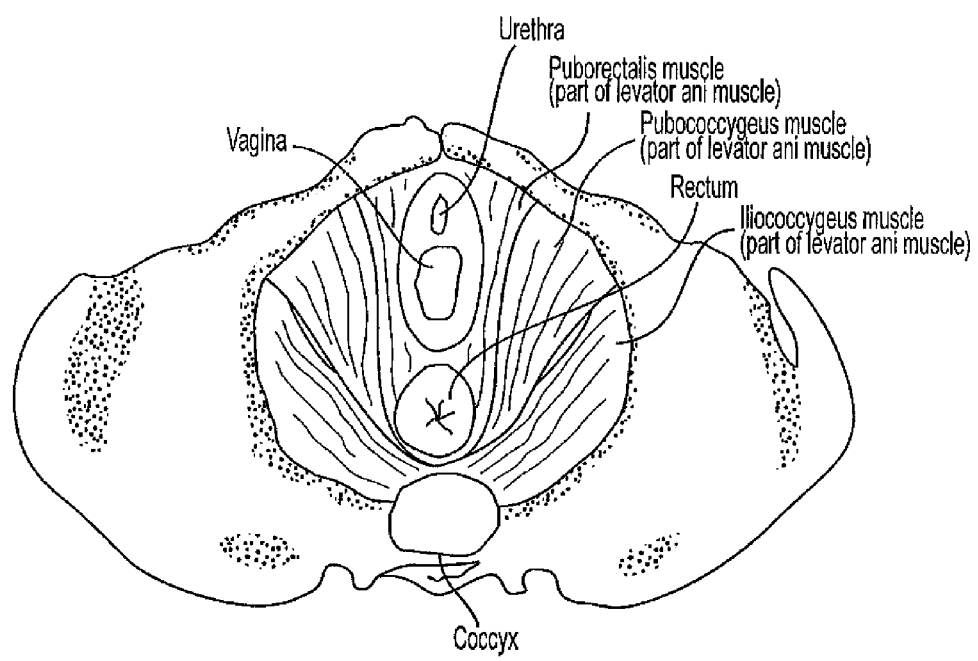
FIG. 1 shows the anatomy of the pelvic floor, including the pubococcygeus muscles and illiococcygeus muscles that make up the levator ani muscles.

Referring now to the drawings, wherein like reference numerals designate identical or corresponding parts throughout the several views. The following description is meant to be illustrative only, and not limiting other embodiments of this invention will be apparent to those of ordinary skill in the art in view of this description.

Figure 2:
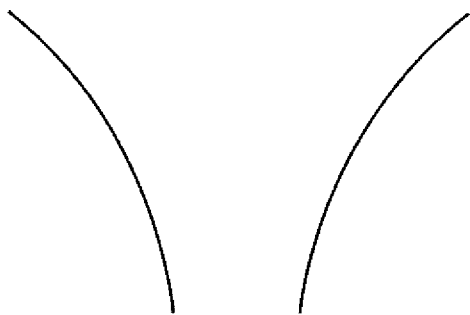
FIG. 2 shows a schematic illustrating the general condition of healthy levator muscles.
Figure 3:
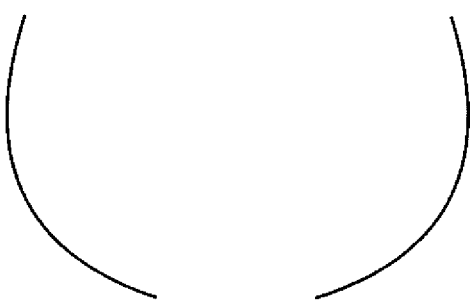
FIG. 3 shows a schematic illustrating the general condition of levators associated with prolapsed pelvic organs.

The relevant anatomy is illustrated in FIG. 1. As can be seen, the levator ani muscles, including the pubococcygeus and illiococcygeus muscles, are a significant portion of the pelvic floor and provide support for the pelvic viscera. FIGS. 1 and 2 show the normal condition of the levator muscles, while FIG. 3 shows the posture of levator muscles associated with prolapsed pelvic organs. As can be seen, such muscles offer less support for the pelvic viscera and may benefit from additional support as provided in the present invention. Further, laxity of such muscles is thought to result in an increased size of the normal opening in the muscles at the urogenital hiatus. With this increased size, there is a tendency of the organs in the anatomical vicinity to fill the opening. This would explain Some degree of prolapse. However, this degree of prolapse caused by the organs filing the open space in the pelvic floor, can lead to increased stress on the normal facsia supports for these organs. This leads to failure of this connective tissue, resulting in further prolapse through the pelvic floor opening.

Figure 4:
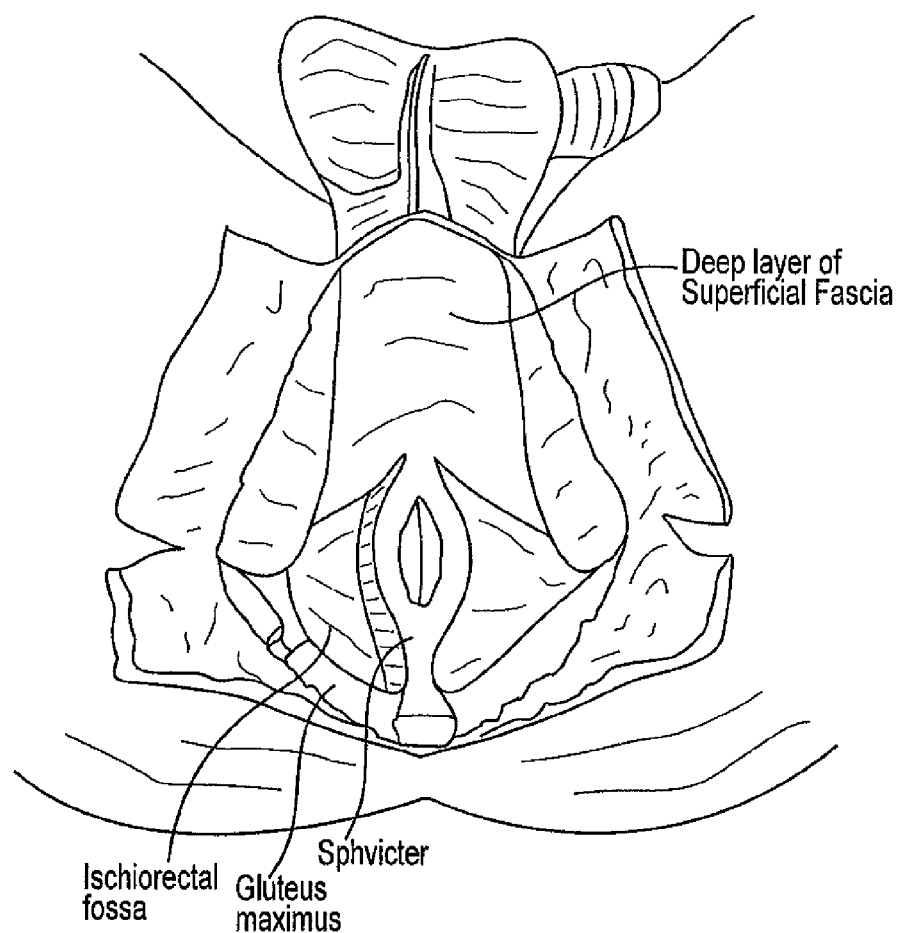
FIG. 4 shows the anatomy of the ischiorectal fossa (though in a male).

In the present invention, an implant is placed in position to support the levator muscle in a tension-free manner. The implant is placed via the ischiorectal fossa. The ischiorectal fossa is seen in FIG. 4. It is somewhat prismatic in shape, with its base directed to the surface of the perineum, and its apex at the line of meeting of the obturator and anal fascia. It is bounded medially by the external anal sphincter and the anal fascia. Laterally, it is bounded by the ischial tuberosity and the obturator fascia. It is bounded anteriorly by the fascia of Colles covering the transverse superficial perineal muscle, and by the inferior fascia of the urogenital diaphragm. Posteriorly, the fossa is bound by the gluteus maximus and the sacrotuberous ligament. Crossing the space transversely are the inferior hemorrhoidal vessels and nerves. At the back part are the perineal and perforating cutaneous branches of the pudendal plexus. From the front, the posterior labial vessels and nerves emerge. The internal pudendal vessels and pudendal nerve lie in Alcock's canal on the lateral wall. The fossa is filled with fatty tissue across which numerous fibrous bands extend from side to side.

Figure 5:
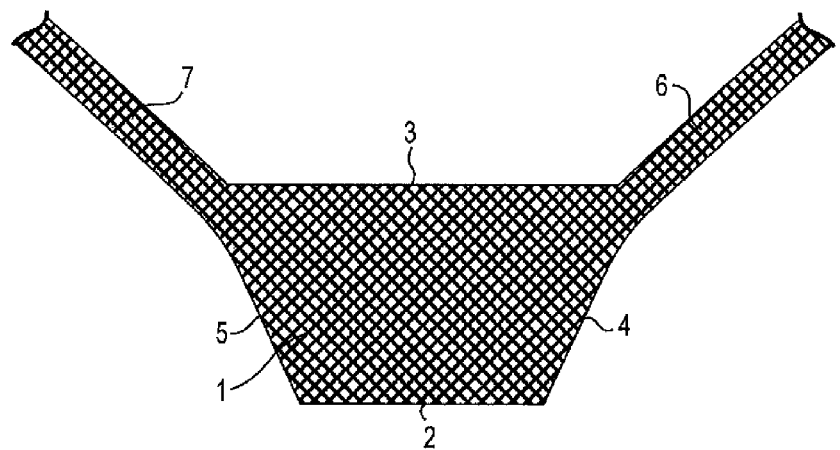
FIG. 5 shows an embodiment of the mesh implant of the present invention.
Figure 6:
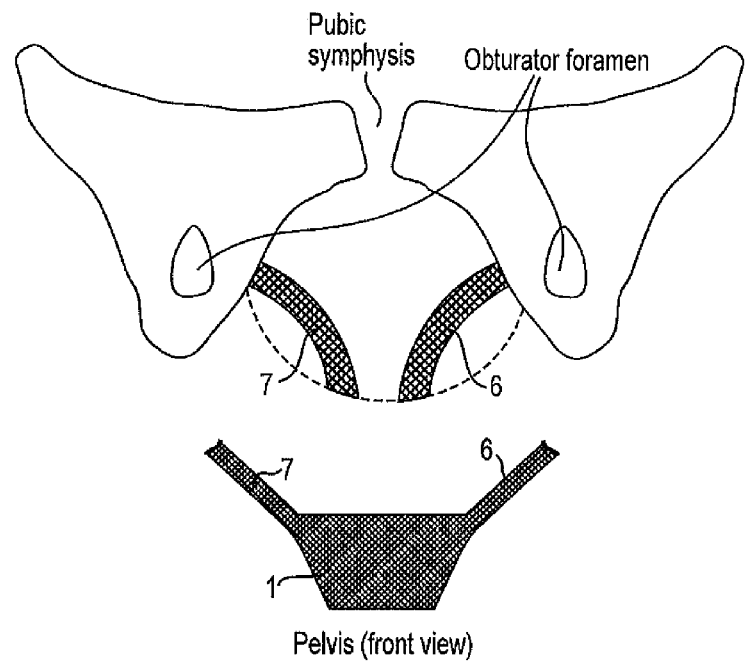
FIG. 6 shows an overview of the anatomical placement of the implant of the present invention.
Figure 7:
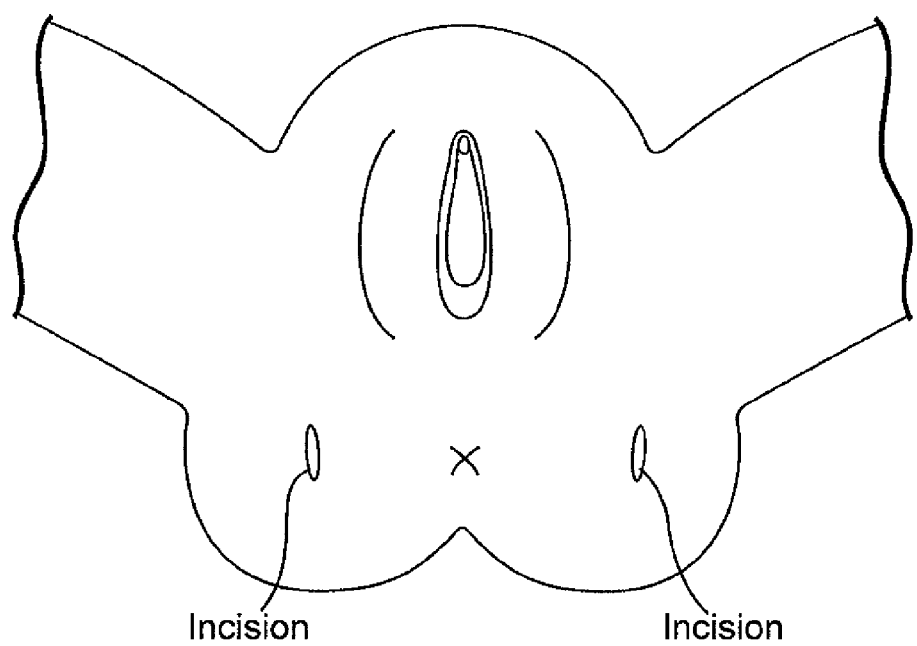
FIG. 7 shows the location of the method of the present invention.
Figure 8:
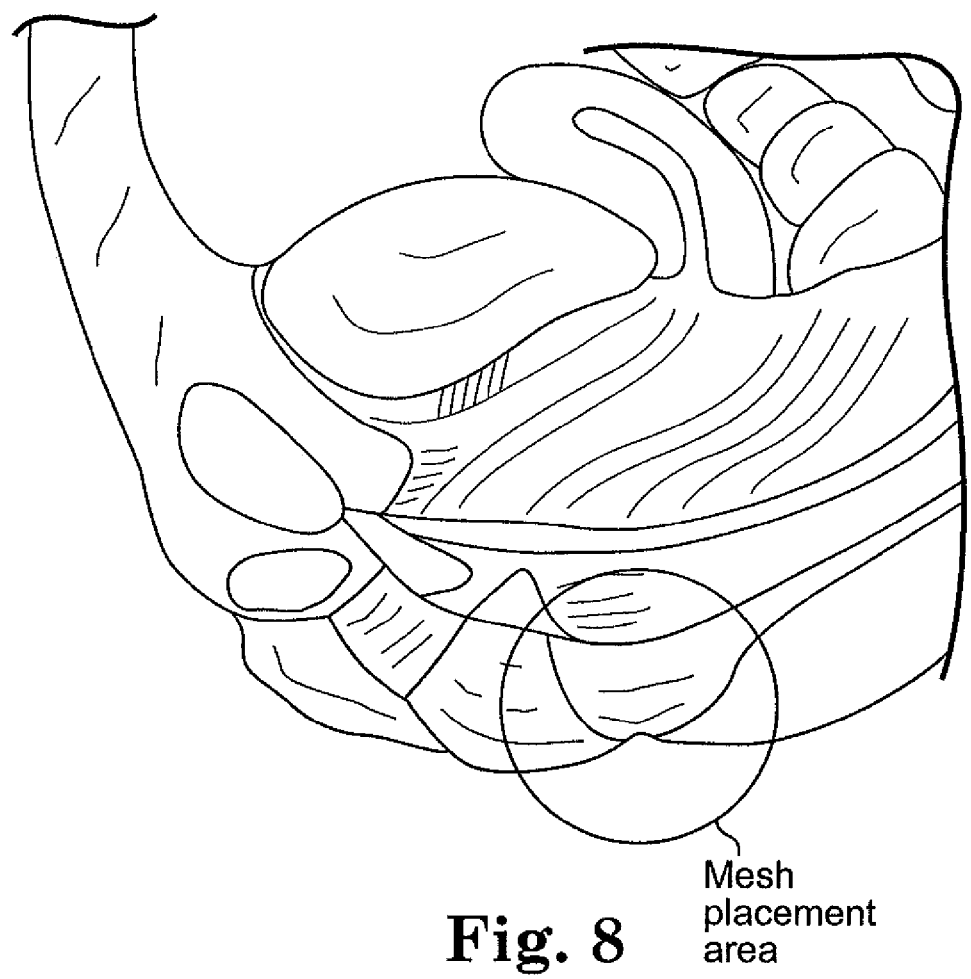
FIGS. 8 and 9 show the anatomical placement of the present invention.
Figure 9:
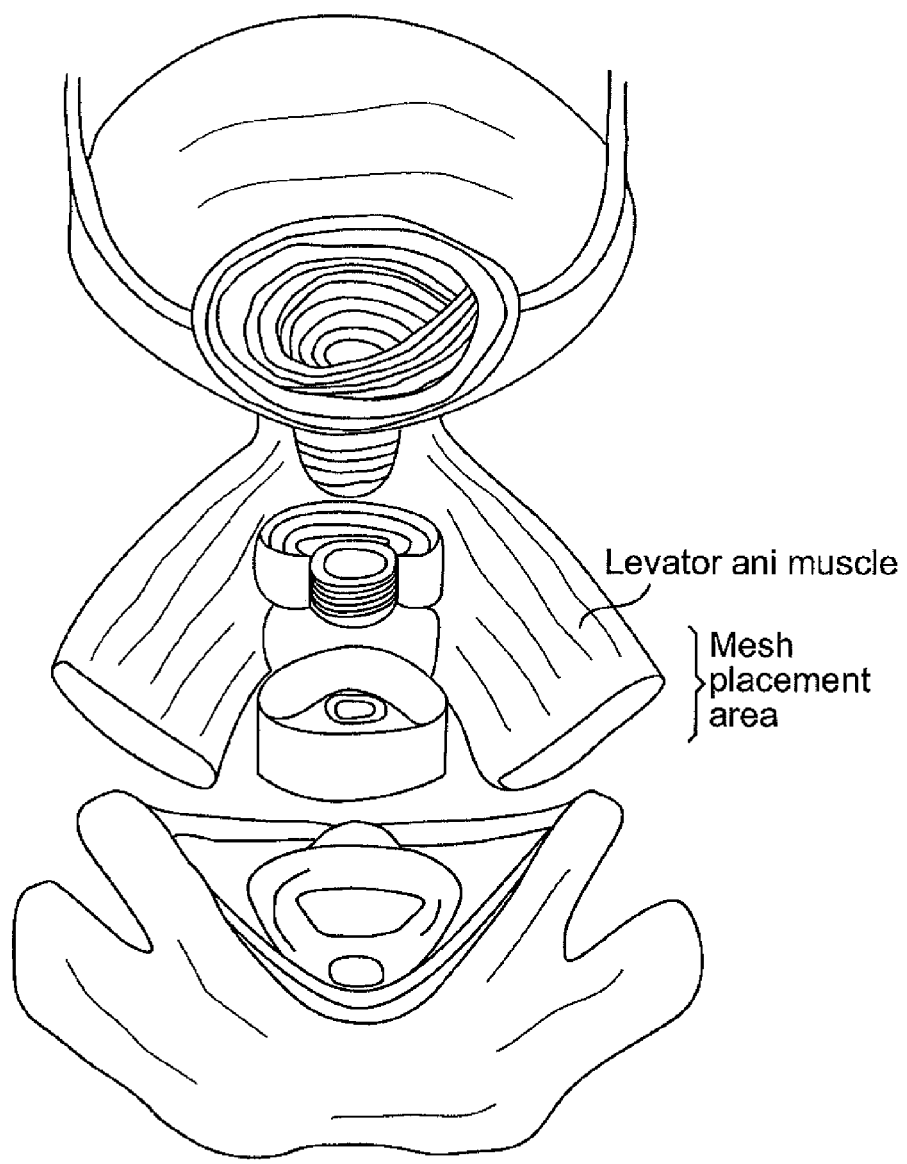

The implant may be of any shape suitable for providing adequate support of the levator musculature. In a preferred embodiment, seen in FIG. 5, the implant includes a central support portion 1 having a trapezoidal shape, with a width of a first side 2 on the base of the trapezoid being less than a width of a second side 3 opposite the base. The implant may have lateral sides 4 and 5 having substantially the same length. The implant preferably comprises a pair of arms 6 and 7 extending from points near the junction of second side 3 and lateral sides 4 and 5, respectively.

The implant of the present invention may be made of a synthetic or non-synthetic material, or a combination thereof. Suitable non-synthetic materials include allografts, homografts, heterografts, autologous tissues, cadaveric fascia, autodermal grafts, dermal collagen grafts, autofascial heterografts, whole skin grafts, porcine dermal collagen, lyophilized aortic homografts, preserved dural homografts, bovine pericardium and fascia lata. Commercial examples of synthetic materials include Marlex™ (polypropylene) available from Bard of Covington, R.I., Prolene™ (polypropylene), Prolene Soft Polypropylene Mesh or Gynemesh (non-absorbable synthetic surgical mesh), both available from Ethicon, of New Jersey, and Mersilene (polyethylene terphthalate) Hernia Mesh also available from Ethicon, Gore-Tex.™ (expanded polytetrafluoroethylene) available from W. L. Gore and Associates, Phoenix, Ariz., and the polypropylene sling available in the SPARC™ sling system, available from American Medical Systems, Inc. of Minnetonka, Minn., Dexon™ (polyglycolic acid) available from Davis and Geck of Danbury, Conn., and Vicryl™ available from Ethicon.

Other examples of suitable materials include those disclosed in published U.S. patent application Ser. No. 2002/0072694, herein incorporated by reference. More specific examples of synthetic materials include, but are not limited to, polypropylene, cellulose, polyvinyl, silicone, polytetrafluoroethylene, polygalactin, Silastic, carbon-fiber, polyethylene, nylon, polyester (e.g. Dacron) polyanhydrides, polycaprolactone, polyglycolic acid, poly-L-lactic acid, poly-D-L-lactic acid and polyphosphate esters. See Cervigni et al., The Use of Synthetics in the Treatment of Pelvic Organ Prolapse, Current Opinion in Urology (2001), 11: 429-435.

U.S. Publication 2005/0245787, U.S. Publication 2005/0250977, U.S. Pat. No. 6,802,807, U.S. Pat. No. 6,911,003, U.S. Pat. No. 7,048,682, and U.S. Pat. No. 6,971,986 are herein incorporated by reference.

Figure 10:
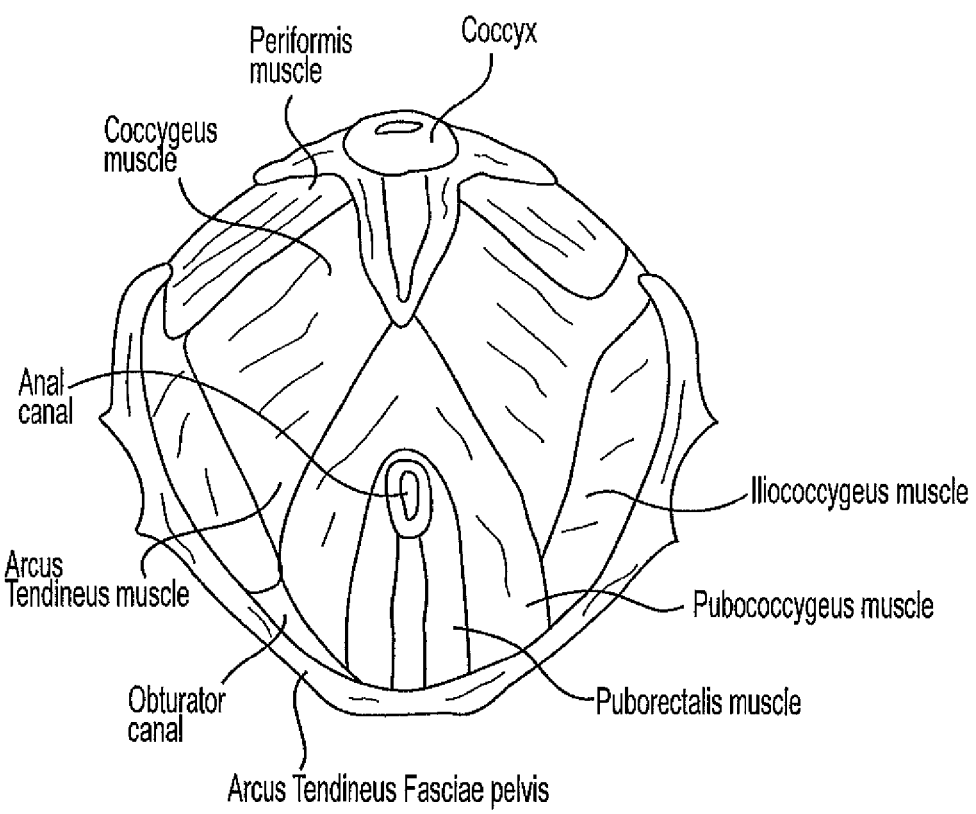
FIG. 10 shows the anatomy of the pelvic floor.

In a preferred embodiment, a suitable delivery needle is attached to a first end portion of said implant. An initial incision is made at a point between the anus and the tip of the coccyx. The relationship between the coccyx and the other structures of the pelvic floor is seen in FIG. 10. Following the incision, the tendon of insertion of the levator ani muscle, at the coccyx, is cut. Following this cut, the surgeon bluntly dissects a space for placement of the present implant lateral to the levator muscles. This dissection may require the use of pillow dissection with placement of a balloon device, followed by inflation of such a balloon to create the required space.

Following the creation of a space on a first side of the levator muscle, the implant of the present invention is attached to a suitable needle. The mesh is placed lateral to the muscle. In a preferred embodiment, the mesh is attached to the obturator internus muscle adjacent to the pubic ramus. The mesh is further attached adjacent the ischial spine into the sacrospinous ligament. The trapezoidal mesh is then draped underneathe the ano-rectal junction into the ischiorectal fossa, emerging on the ocontralateral side of the first and second attachments. The mesh implant is then attached to the obturator internus muscle adjacent to the pubic ramus on the contralateral side of the patient, and adjacent the ischial spine into the sacrospinous ligament on the contralateral side.

Obviously, numerous modifications and variations of the present invention are possible in light of the above teachings. It is therefore to be understood that within the scope of the appended claims, the invention may be practiced otherwise than as specifically described herein.

The invention claimed is:

1. A method of treating pelvic organ prolapse, said method comprising the placement of an implant via ischiorectal fossa to provide support for levator ani muscle, wherein the implant comprises a center support portion comprising a long side and a short side, the long side and the short side being substantially parallel, and lateral sides extending between the long side and the short side, and each arm extending from a corner between the long side and a lateral side, and two arms,
   the method comprising
   making an incision between an anus and a tip of a coccyx,
   placing the implant through the incision,
   placing a portion of the center support portion lateral and adjacent to iliococcygeus muscle, via ischiorectal fossa, on one side of the patient,
   placing a portion of the center support portion lateral and adjacent to iliococcygeus muscle, via ischiorectal fossa, on the other side of the patient, and
   connecting each arm to an obturator internus muscle adjacent to a pubic ramus, wherein the method comprises supporting disrupted or lax levator muscles to prevent or limit descent or lateral displacement of levator muscle.

2. The method of claim 1 wherein the arms are substantially aligned with the lateral sides.

3. The method of claim 1 for the treatment of descending perineum syndrome.

4. The method of claim 1 wherein the implant is draped underneath the ano-rectal junction into the ischiorectal fossa.

5. The method of claim 1 wherein a ratio between a length of the long side and a length of the short side is about 5:2.

6. The method of claim 1 wherein the long side of the center support portion has a length of about 5 cm, the short side has a length of about 2 cm, and the lateral sides of the center support portion have a length of about 8 cm.

7. A method of treating pelvic organ prolapse, the method comprising:
   creating an incision between an anus and a tip of a coccyx,
   dissecting to access levator muscle on both sides of the patient, and dissecting space lateral to levator muscle on both sides of the patient,
   placing an implant comprising a center support portion and two arms by placing a portion of the center support portion lateral and adjacent to iliococcygeus muscle, via ischiorectal fossa, on one side of the patient, the implant comprising
      a center support portion and two arms, the center support portion comprising a trapezoid having
         a long side and a short side, the long side and the short side being substantially parallel, and
         lateral sides extending between the long side and the short side,
         two anterior corners, one each between the long side and one of the two lateral sides, and
         two posterior corners, one each between the short side and one of the two lateral sides,
      wherein each arm extends from an anterior corner,
   placing a portion of the center support portion lateral and adjacent to iliococcygeus muscle, via ischiorectal fossa, on the other side of the patient,
   connecting each arm to an obturator internus muscle adjacent to a pubic ramus, and
   connecting each posterior corner to sacrospinous ligament adjacent an ischial spine.

8. The method of claim 7 comprising supporting disrupted or lax levator muscles to prevent or limit descent or lateral displacement of levator muscle.

9. The method of claim 7 for the treatment of descending perineum syndrome.

10. The method of claim 7 wherein the implant is draped underneath the ano-rectal junction.

11. The method of claim 7 wherein a ratio between a length of the long side and a length of the short side is about 5:2.

12. The method of claim 7 wherein the long side of the center support portion has a length of about 5 cm, the short side has a length of about 2 cm, and the lateral sides of the center support portion have a length of about 8 cm.

13. A method of treating pelvic organ prolapse, said method comprising the placement of an implant via ischiorectal fossa to provide support for levator ani muscle, wherein the implant comprises a center support portion and two arms, the method comprising
   making an incision between an anus and a tip of a coccyx,
   placing the implant through the incision,
   placing a portion of the center support portion lateral and adjacent to iliococcygeus muscle, via ischiorectal fossa, on one side of the patient,
   placing a portion of the center support portion lateral and adjacent to iliococcygeus muscle, via ischiorectal fossa, on the other side of the patient, and
   connecting each arm to an obturator internus muscle adjacent to a pubic ramus, wherein the method comprises supporting disrupted or lax levator muscles to prevent or limit descent or lateral displacement of levator muscle, and
   connecting the implant to a sacrospinous ligament adjacent to an ischial spine.

* * * * *